United States Patent [19]

Karaki

[11] Patent Number: 4,459,986

[45] Date of Patent: Jul. 17, 1984

[54] SURGICAL LASER SYSTEM

[75] Inventor: Kouichi Karaki, Hachioji, Japan

[73] Assignee: Olympus Optical Co. Ltd., Japan

[21] Appl. No.: 347,298

[22] Filed: Feb. 9, 1982

[30] Foreign Application Priority Data

Feb. 16, 1981 [JP] Japan ............................ 56-20226

[51] Int. Cl.³ ............................................. A61B 17/36
[52] U.S. Cl. .................... 128/303.1; 128/395; 219/121 LZ
[58] Field of Search ......... 128/303.1, 303 R, 395–398; 219/121 L, 121 LM, 121 LQ, 121 LR, 121 LZ; 372/36; 350/6.5, 6.9–6.91

[56] References Cited

U.S. PATENT DOCUMENTS

| | | | |
|---|---|---|---|
| 2,710,798 | 6/1955 | Hansley | 75/66 |
| 3,062,965 | 11/1962 | Sick | 350/6.91 X |
| 3,528,424 | 9/1970 | Ayres | 128/303.1 |
| 3,710,798 | 1/1973 | Bredemeier | 128/303.1 |
| 3,865,114 | 2/1975 | Sharon | 128/303.1 |
| 4,266,547 | 5/1981 | Komiya | 128/303.1 |
| 4,423,726 | 1/1984 | Imagawa et al. | 128/303.1 |

FOREIGN PATENT DOCUMENTS 2832847  2/1980  Fed. Rep. of Germany ... 128/303.1

Primary Examiner—Lee S. Cohen
Assistant Examiner—Angela D. Sykes
Attorney, Agent, or Firm—Parkhurst & Oliff

[57] ABSTRACT

An amount of energy of an output laser beam emanating from a distal end of a flexible light guide is measured by arranging a partial reflecting mirror having a reflection factor of about 99% and a transmissivity of about 1% at the last rotating nod portion of the light guide nearest to the distal end. A heat sink is applied onto a rear surface of the partial reflecting mirror and a thermocouple is arranged in contact with the heat sink to measure a temperature of the heat sink. The output energy of the laser beam can be accurately measured from an output signal of the thermocouple without being affected by a variation of a transmissivity of the light guide.

11 Claims, 6 Drawing Figures

SURGICAL LASER SYSTEM

BACKGROUND OF THE INVENTION

The present invention relates to a surgical laser system, and more particularly to an apparatus for detecting an amount of output energy of a laser beam at a distal end of the surgical laser system.

The surgical laser system has been known from, for instance, U.S. Pat. No. 3,710,798. Such a known surgical laser system is advantageously used clinically for delicate operations including cutting, coagulation and vaporization. The surgical laser system comprises a laser light source such as $CO_2$ gas laser producing a high energy laser beam, a flexible light guide tube having a distal end for emitting the laser beam toward an operating site. In such a surgical laser system, in order to effect the operation efficiently, it is important to measure the amount of energy of laser beam impinging upon the operating site. For this purpose, in the known system a part of the laser beam impinging upon an incident end of the light guide is derived and is made incident upon a light detector such as a heat sink. The laser beam impinging upon the heat sink is converted into a heat energy and by measuring the temperature of the heat sink the amount of the laser beam incident upon the light guide is detected. Then the amount of energy of the laser beam impinging upon the operating site is calculated with taking into account a transmissivity of the light guide. Such an indirect measuring system cannot have a high accuracy due to a fluctuation of transmissivity of the light guide.

In another known measuring system, the output laser beam emanating from the distal end of light guide is directly measured by introducing the output laser beam into a power meter. By means of such a direct measuring system, it is possible to detect directly the output energy of the laser beam and thus, a very high accuracy can be obtained. However in such a system, the energy of the laser beam impinging upon the operating site cannot be measured in real time. In other words, during the actual operation, the energy of the laser beam could not be detected. Therefore, if the energy of the laser beam is varied abruptly due to the fluctuation of the laser light source and the transmissivity of the light guide, such a variation of laser beam could not be detected. Further, the operation must be interrupted frequently by the measurement of the laser output energy.

SUMMARY OF THE INVENTION

The present invention has for its object to provide a novel and useful apparatus for measuring precisely an amount of a laser light beam at a distal end of a light guide in a real time without interrupting operations.

According to the invention, an apparatus for measuring an amount of energy of an output laser beam at a distal end of light guide of a surgical laser system comprises means arranged near the distal end of the light guide for separating a small part of the laser beam transmitted through the light guide; and means for receiving said small part of the laser beam to measure the energy of the output laser beam emanating from the distal end of the light guide.

DESCRIPTION OF THE PREFERRED EMBODIMENTS

Figure 1:
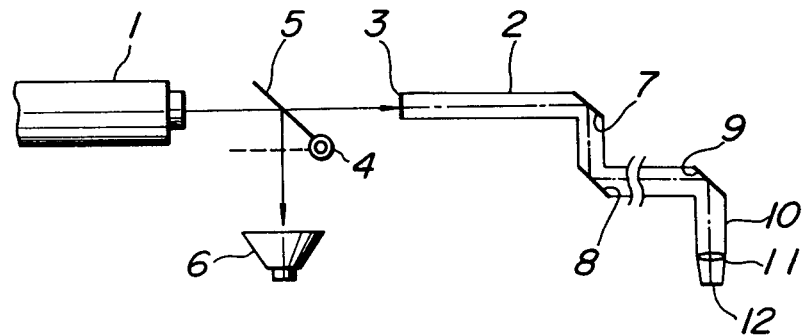
FIG. 1 is a schematic view showing a known surgical laser system.

FIG. 1 is a cross sectional view showing a known surgical laser system. In the known system, in order to measure the energy of an output laser beam, between a laser light source 1 and an incident end 3 of a light guide 2 is arranged a reflection mirror 5 rotatably journaled by a shaft 4. In case of measuring the laser beam energy, the mirror 5 is inserted into an optical axis and the laser beam is reflected by the mirror toward a heat sink 6. The laser beam impinging upon the heat sink 6 is converted into an electrical signal which is then indicated by a power meter not shown.

The light guide 2 comprises a plurality of tubes rotatably coupled with each other in series and at each junction point reflection mirrors 7, 8 and 9 are provided. The laser beam impinging upon the entrance 3 is transmitted through the tubes and is introduced into a hand piece 10 including an objective lens 11. The laser beam focussed by the objective lens 11 is projected through an exit end or distal end 12 of the light guide 2 onto an operating site.

In such a known system, the laser beam power is detected at the entrance of the light guide and the energy of the output laser beam emanating from the distal end 12 is calculated by multiplying the measured energy by a transmissivity of the light guide 2 which has been previously measured. In practice, the multiplying is effected by an operator or his assistant manually or by a microcomputer automatically. However, such a measuring method is affected by a variation in the transmissivity of the light guide 2. For instance, the transmissivity of the light guide might be varied due to damage of an optical fiber or manipulator constituting the light guide, misalignment of the reflection mirrors, etc.

Figure 2:
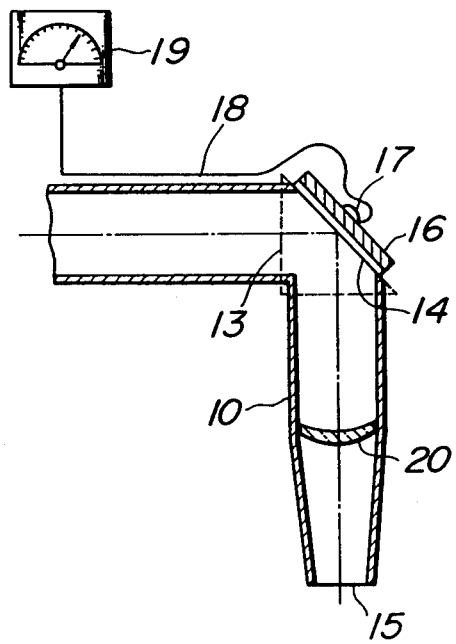
FIG. 2 is a cross sectional view illustrating an embodiment of the apparatus according to the invention.

FIG. 2 is a cross sectional view showing an embodiment of the measuring apparatus according to the invention. In this embodiment, a partial reflecting mirror 14 is arranged at a rotating nod portion in a hand piece 10 of the manipulator. The partial reflecting mirror 14 is so constructed that a substantial large part of the incident laser beam is reflected toward a distal end 15 and a very small part of the incident laser beam is transmitted through the partial reflecting mirror 14. The transmitted laser beam is made incident upon a heat sink 16. In this manner, an energy of the laser beam is converted into a thermal energy by the heat sink 16. Then the temperature of the heat sink 16 is measured by a thermo-electric element such as a thermocouple 17. The thermocouple 17 is connected to an indicator 19 via a conductor 18 arranged along manipulator constituting the light guide. The indicator 19 has been so calibrated that the amount of the output laser beam emanating from the exit end 15 is indicated in accordance with the electrical siganl supplied from the thermocouple 17. The laser beam reflected by the mirror 14 is focussed by an objective lens 20 and is projected through the exit end 15 onto an operating site.

The partial reflecting mirror 14 has a very high reflection factor of 99% and a very low transmissivity of 1%. Such a partial reflecting mirror can be manufactured by multiple coatings of dielectric films.

In this embodiment, a very small part of the laser beam is separated at the hand piece 10 constituting the last stage of the manipulator and is detected by the light energy detecting element comprising the heat sink 16 and thermocouple 17. Therefore, if the amount of the laser beam is fluctuated by abnormality of the optical system including the reflection mirrors inserted in the light guide up to the hand piece 10, the amount of the laser beam impinging upon the partial reflection mirror 14 is varied accordingly. In this manner, the abnormality of the laser beam can be accurately detected during the operation.

It should be noted that since the partial reflecting mirror is sufficient to have the transmissivity of about 1%, the energy absorbed by the heat sink 16 is about 1W even if the laser light source has an output energy of about 100W, it is unnecessary to cool the heat sink 16.

Figure 3:
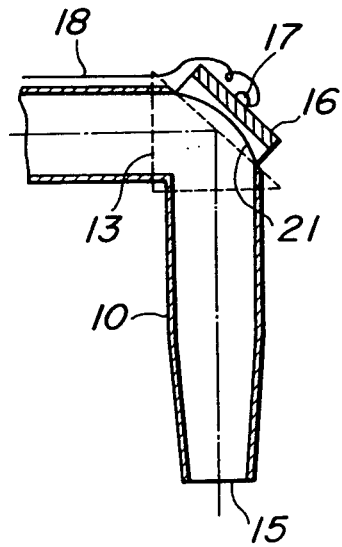
FIG. 3 is a cross sectional view showing a modified embodiment of the apparatus shown in FIG. 2.

FIG. 3 is a cross section illustrating a modified embodiment of the apparatus shown in FIG. 2. Portions in FIG. 3 similar to those shown in FIG. 2 are denoted by the same reference numerals used in FIG. 2. In this embodiment, a partial reflecting mirror 21 is formed as a concave reflecting mirror for focussing the laser beam toward the exit end 15. Therefore, the objective lens provided in the embodiment shown in FIG. 2 can be omitted. The light energy detecting element comprises a heat sink 16 and a thermocouple 17. The heat sink 16 is made in contact with the partial reflecting mirror 21 to receive a very small part of the laser beam transmitted through the mirror 21.

In this embodiment, since there is no optical system such as an objective lens from the beam separating element, i.e. the partial reflecting mirror 21 to the exit end 15, the much more accurate measurement can be effected without being affected by loss, damage or blur of the objective lens.

Figure 4:
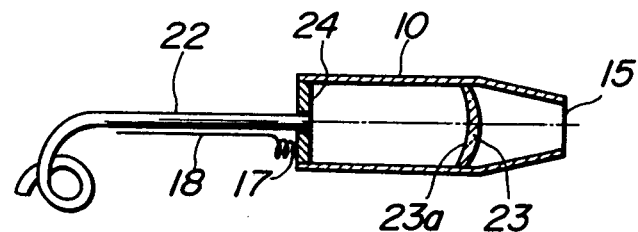
FIG. 4 is a cross sectional view depicting another embodiment of the apparatus according to the invention.

FIG. 4 is a cross sectional view illustrating another embodiment of the apparatus according to the invention which is preferable to be applied to surgical laser system comprising a light guide consisting of an optical fiber. In the present embodiment, the light guide is composed of a flexible optical fiber 22 and a hand piece 10 coupled with one end of the optical fiber 22, the other end of optical fiber being optically coupled with the laser light source. The optical fiber 22 may be made of a quartz fiber. In the hand piece 10 is arranged an objective lens 23 having a partial reflecting surface 23a. A very small part of the laser beam emitted from the optical fiber 22 is reflected by the surface 23a backwards. Almost all laser beam is transmitted through the objective lens 23 and is focussed through the outlet 15 onto the operating site. The reflecting surface 23a has a transmissivity of about 99% and a reflection factor of about 1%. The small part of the laser beam reflected by the surface 23a is made incident upon a heat sink 24 which also serves to support the optical fiber 22. The temperature of the heat sink 24 is detected by a thermocouple 17 and an electrical output signal from the thermocouple 17 is supplied to an indicator by means of a conductor 18. In this embodiment, since the reflecting surface 23a of objective lens 23 is so curved to condense the reflected light beam toward the heat sink 24, the very high efficiency can be obtained.

Figure 5:
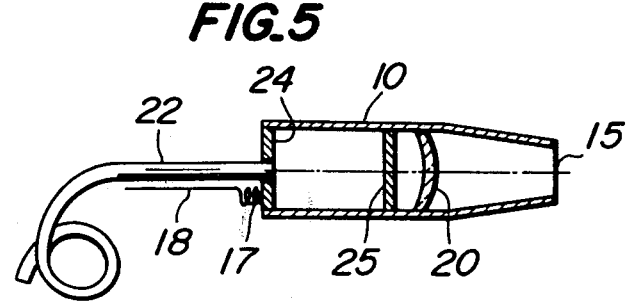
FIGS. 5 and 6 are cross sectional views showing two modified embodiments of the apparatus illustrated in FIG. 4.
Figure 6:
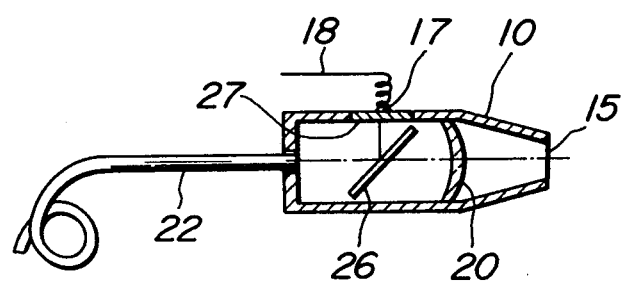

FIGS. 5 and 6 show modified embodiments of the apparatus shown in FIG. 4. In the embodiment illustrated in FIG. 5, a partial reflecting mirror 25 is arranged separately from an objective lens 20 in a hand piece 10 of a light guide. A very small part of the laser beam is reflected by the partial mirror 25 toward a heat sink 24. In the embodiment shown in FIG. 6, a plane partial reflecting mirror 26 is arranged in a hand piece 10 with being inclined with respect to an optical axis by about 45° and a heat sink 27 is arranged in the hand piece 10 at such a position that a very small part of the laser beam reflected by the partial reflecting mirror 26 is received by the heat sink 27. In this embodiment, the heat sink 27 constitutes a part of the housing of the hand piece 10. A very large amount of the laser beam transmitted through the partial reflecting mirror 27 is focussed by an objective lens 20.

What is claimed is:

1. An apparatus for measuring an amount of energy in an output from a laser beam in a surgical laser system, including a laser light source and a light guide, the light guide having a plurality of tubes rotatably coupled together at portions occurring between successive tubes and a plurality of reflecting mirrors arranged at the rotatably coupled portions occurring between successive tubes, said light guide transmitting a laser beam emitted from the laser light source toward an operating site, comprising;

transmission means, provided on a last reflecting mirror arranged at a distal end of the light guide, for transmitting a very small part of the laser beam through the last reflecting mirror;

receiving means including a heat sink located on a rear surface of the last reflecting mirror for receiving the very small part of the laser beam transmitted through the last reflecting mirror; and measurement means including a temperature measuring element for measuring a temperature of the heat sink.

2. The apparatus of claim 1, wherein the transmission means provided on the last reflecting mirror is a coating of at least one coat of dielectric film.

3. The apparatus of claim 1, wherein said temperature measuring element comprises a thermocouple applied to said heat sink.

4. The apparatus of claim 1, wherein said last reflecting mirror has a reflection factor of about 99% and a transmissivity of about 1%.

5. The apparatus of claim 1, wherein said last reflecting mirror is a plane mirror.

6. The apparatus of claim 1, wherein said last reflecting mirror is a concave mirror which focusses and projects the laser beam through the distal end of the light guide.

7. An apparatus for measuring an amount of energy in an output from a laser beam is a surgical laser system, including a laser light source and a light guide, the light guide having an optical fiber with a first end optically coupled with the laser light source and a second end coupled to a hand piece, the hand piece including an objective lens for converging the laser beam emitted from the first end of the optical fiber toward an operating site, comprising;

a partial reflecting coating applied on an incident surface of the objective lens for reflecting a very small amount of the laser beam incident upon the objective lens;
   heat sink means arranged in the hand piece for receiving the reflected laser beam; and
   a temperature measuring element means for measuring a temperature of the heat sink.

8. The apparatus of claim 7, wherein said lens surface is concave and said heat sink is arranged at an incident side of the hand piece to hold said second end of the optical fiber.

9. The apparatus of claim 7, wherein said heat sink forms a part of a housing of the hand piece.

10. An apparatus for measuring an amount of energy in an output from a laser beam and a surgical laser system, including a laser light source and a light guide, the light guide having an optical fiber with a first end optically coupled with the laser light source said laser beam being emitted from the first end of the optical fiber, and a second end coupled to a hand piece including an objective lens for converging the laser beam emitted from the first end of the optical fiber toward an operating site comprising;
   a planar mirror having a partial reflecting coating applied on a laser incident for reflecting a very small amount of the laser beam incident upon the planar mirror, the planar mirror being located optically upstream from the objective lens;
   heat sink means arranged in the hand piece for receiving the reflected laser beam; and
   temperature measuring element means for measuring a temperature of the heat sink.

11. The apparatus of claim 10, wherein the planar mirror is arranged in an inclined fashion with respect to an optical axis and the heat sink means is positioned in a side wall of the hand piece.

* * * * *